United States Patent [19]

Rolf et al.

[11] Patent Number: 5,536,263

[45] Date of Patent: Jul. 16, 1996

[54] NON-OCCULUSIVE ADHESIVE PATCH FOR APPLYING MEDICATION TO THE SKIN

[75] Inventors: David Rolf, Minneapolis; Elisabeth K. S. Urmann, St. Paul, both of Minn.

[73] Assignee: Lectec Corporation, Minnetonka, Minn.

[21] Appl. No.: 219,982

[22] Filed: Mar. 30, 1994

[51] Int. Cl.⁶ ........................................ A61F 13/00
[52] U.S. Cl. .................. 604/307; 424/449; 424/447; 604/304; 314/953; 314/965; 602/48
[58] Field of Search ................... 604/304, 307; 602/48–51; 424/447–449; 514/953, 964, 965

[56] References Cited

U.S. PATENT DOCUMENTS

| | | | |
|---|---|---|---|
| 2,137,169 | 11/1938 | Leven | 167/84 |
| 3,249,109 | 5/1966 | Maeth et al. | 128/268 |
| 3,339,546 | 9/1967 | Chen | 128/156 |
| 3,428,043 | 2/1969 | Sheperd | 128/268 |
| 3,598,122 | 8/1971 | Zaffaroni | 128/268 |
| 3,612,053 | 10/1971 | Pratt | 128/283 |
| 3,640,741 | 2/1972 | Etes | 106/170 |
| 3,731,683 | 5/1973 | Zaffaroni | 128/268 |
| 3,742,951 | 7/1973 | Zaffaroni | 128/268 |
| 3,767,784 | 10/1973 | Gluck | 424/28 |
| 3,814,095 | 6/1974 | Lubens | 128/260 |
| 3,972,995 | 8/1976 | Tsuk et al. | 424/28 |
| 3,998,215 | 12/1976 | Anderson et al. | 128/2.06 E |
| 4,002,221 | 1/1977 | Buchalter | 181/05 |
| 4,089,329 | 5/1978 | Couvillon, Jr. et al. | 128/2 T |
| 4,125,110 | 11/1978 | Hymes | 128/206 E |
| 4,253,460 | 3/1981 | Chen et al. | 128/283 |
| 4,274,420 | 6/1981 | Hymes | 128/641 |
| 4,299,231 | 11/1981 | Karmann et al. | 128/639 |
| 4,306,551 | 12/1981 | Hymes et al. | 128/156 |
| 4,307,717 | 12/1981 | Hymes et al. | 128/156 |
| 4,457,748 | 7/1984 | Lattin et al. | 604/20 |
| 4,474,570 | 10/1984 | Ariura et al. | 604/20 |
| 4,515,162 | 5/1985 | Yamamoto et al. | 128/640 |
| 4,585,652 | 4/1986 | Miller et al. | 424/83 |
| 4,593,053 | 6/1986 | Jevne et al. | 523/111 |
| 4,638,043 | 1/1987 | Szycher et al. | 528/75 |
| 4,675,009 | 6/1987 | Hymes et al. | 604/304 |
| 4,692,273 | 8/1987 | Lawrence | 252/518 |
| 4,694,835 | 9/1987 | Strand | 128/640 |
| 4,696,854 | 9/1987 | Ethier | 428/287 |
| 4,702,732 | 10/1987 | Powers et al. | 604/20 |

(List continued on next page.)

OTHER PUBLICATIONS

External Analgesic Drug Products for Over-the-Counter Use; Tentative Final Monograph, Federal Register, Tuesday, Feb. 8, 1983 (19 pages).

*Primary Examiner*—Randall L. Green
*Assistant Examiner*—Robert Clarke
*Attorney, Agent, or Firm*—James V. Warmon

[57] ABSTRACT

A non-occlusive medication patch to be applied to the skin includes a porous self-supporting backing layer to give the patch the required integrity and strength by acting as a supporting framework for other components, and a flexible hydrophilic pressure-sensitive adhesive reservoir comprising a hydrocolloidal gel for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication-containing reservoir. The medication within the reservoir migrates over time from within the backing through the lower coating layer and passes through the skin to provide sustained release of the medication into the body of a patient. The reservoir comprises a hydrocolloidal dispersion of a natural or synthetic gel-forming polymer, a hydrophilic adhesive, a hydrophilic humectant and a biomedically active medication, i.e., a medicament, dispersed throughout the reservoir including both the external portion and the internal portion that infiltrates the porous backing.

24 Claims, 1 Drawing Sheet

U.S. PATENT DOCUMENTS

| | | | |
|---|---|---|---|
| 4,704,282 | 11/1987 | Campbell et al. | 424/449 |
| 4,717,378 | 1/1988 | Perrault et al. | 604/20 |
| 4,778,786 | 10/1988 | Reever et al. | 514/54 |
| 4,989,607 | 2/1991 | Keusch et al. | 128/640 |
| 5,002,792 | 3/1991 | Vegoe | 427/2 |
| 5,123,423 | 6/1992 | Schamberg | 128/798 |
| 5,142,817 | 9/1992 | Rolf | 47/24 |
| 5,205,297 | 4/1993 | Montecalvo et al. | 128/798 |
| 5,224,967 | 7/1993 | Rolf et al. | 47/58 |

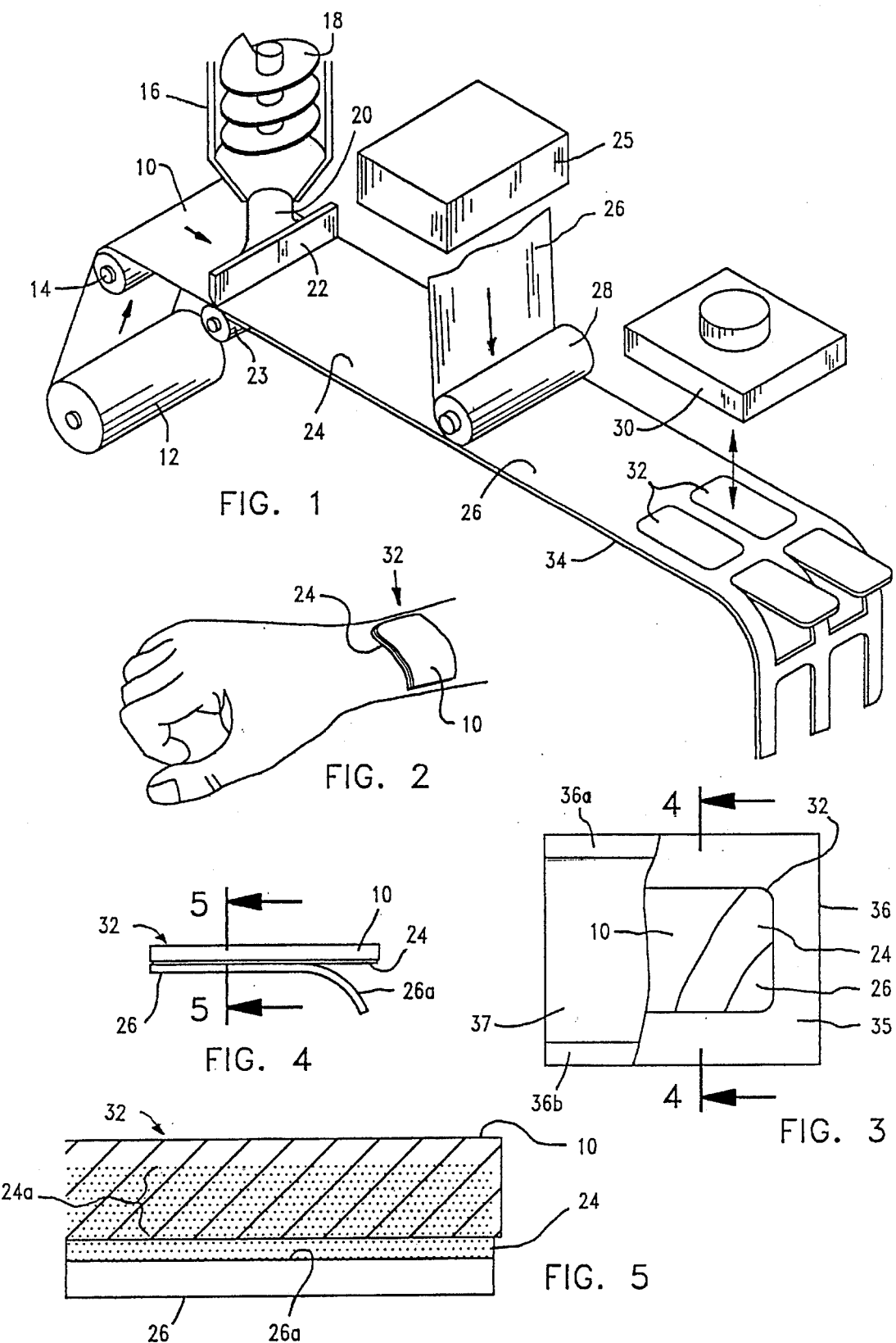

NON-OCCLUSIVE ADHESIVE PATCH FOR APPLYING MEDICATION TO THE SKIN

FIELD OF THE INVENTION

This invention relates to an improved non-occlusive hydrocolloidal adhesive patch for applying medication to the skin.

BACKGROUND OF THE INVENTION

Several kinds of patch devices have been used in the past for applying medication to the skin. For example, pat. 4,675,009 describes a drug dispensing device for transdermal delivery of medication in which a natural or synthetic polysaccharide or synthetic polymer functions as a non-biodegradable adhesive reservoir. These patches, while very good, are so thick and cumbersome that users complain of their appearance and the discomfort associated with their use. Another deficiency is found in analgesic patch products that contain a rubber sheet backing which occludes the skin, making moisture evaporation virtually impossible.

One important object of the present invention is to provide a non-occlusive analgesic patch, i.e., one which will enable moisture vapor on the surface of the skin to evaporate through the patch so as to prevent the undesired accumulation of moisture which, if it occurred, could cause the patch to fall off or even facilitate the growth of bacteria beneath the patch.

Another objective of the present invention is to provide a much lighter, more flexible and less obtrusive patch while still providing excellent sustained release properties during eight hours or more of use.

Another more specific object is to find a way to enable the backing of the adhesive tape itself to serve as a reservoir for the sustained release of a medication to be applied topically into the skin.

Still another more specific object is to unify a porous backing and a hydrophilic pressure-sensitive hydrocolloidal dispersion which serves as a reservoir for medication so as to provide sustained release of the medication while reducing the thickness and bulk of the patch and improving its flexibility.

A further more specific object of the present invention is to provide a more comfortable and less obtrusive topical analgesic patch for the temporary relief of pain including arthritis pain, backaches as well as muscular aches and strains.

Yet another object is to provide an improved method of combining the porous backing and the hydrocolloidal medication-containing pressure-sensitive adhesive reservoir during manufacture.

These and other more detailed and specific objects of the present invention will be better understood by reference to the following figures and detailed description which illustrate by way of example but a few of the various forms of the invention within the scope of the appended claims.

SUMMARY OF THE INVENTION

Briefly, the present invention provides a non-occlusive medication patch to be applied to the skin. It includes a porous self-supporting backing layer to give the patch the required integrity and strength by acting as a supporting framework for other components, and a flexible hydrophilic pressure-sensitive adhesive reservoir comprising a hydrocolloidal gel for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication-containing reservoir. In this way, the medication within the reservoir migrates over time from within the backing through the lower coating layer and passes through the skin to provide sustained release of the medication into the body of a patient.

The reservoir comprises a hydrocolloidal dispersion of a natural or synthetic gel-forming polymer, a hydrophilic adhesive, a hydrophilic humectant and a biomedically active medication, i.e., a medicament, dispersed throughout the reservoir including both the external portion and the internal portion that infiltrates the porous backing.

The invention provides a comfortable, highly flexible patch that is thinner than prior patches, conforms to the body contours, is better tolerated by patients, and is considered by patients to be more unobtrusive. The invention provides outstanding results as a non-occlusive analgesic patch that can be adhered to the skin to release an analgesic for the relief of pain including arthritis pain, backache as well as muscular aches and strains. In such an application, the analgesic comprises trolamine salicylate, menthol salicylate, menthol, camphor, eucalyptus oil or spearmint oil, or a combination thereof.

The invention will be better understood by reference to the following specification and accompanying drawings.

THE FIGURES

FIG. 1 is a perspective diagrammatic view illustrating a preferred method of forming products in accordance with the invention;

FIG. 2 is a perspective view of the improved medication patch applied to the body;

FIG. 3 is a plan view showing the medication patch packaged within in a pouch used as a shipping package;

FIG. 4 is a cross-sectional view of the medication patch taken on line 4—4 of FIG. 3 with a portion of the liner sheet partially removed; and FIG. 5 is a greatly enlarged microscopic view of the medication patch and liner sheet taken on line 5—5 of FIG. 4.

DETAILED DESCRIPTION OF THE INVENTION

Refer now to FIG. 1 which illustrates diagrammatically the production of medication-applying patches in accordance with the invention. The backing sheet 10 is unwound continuously from a supply roll 12, passes upwardly in the figure over an idler roll 14 and then travels horizontally beneath a continuous processing mixer 16 where freshly prepared fluid hydrogel material at 20 is applied to the upper surface of the backing sheet 10.

The backing 10 is a porous self-supporting sheet of water insoluble polymeric material that provides strength and integrity for the adhesive patch as well as acting as a substrate for receiving and retaining a portion of the liquid hydrogel as will be described below.

One preferred backing sheet 10 is a lightweight, pliable strip composed, for example, from a nonwoven fabric which consists of polymeric fibers such as polyester, cotton or cellulose fibers bonded together with a sizing resin. The backing sheet 10 should be nonirritating to human skin. If desired, the backing sheet 10 can be coated on its back surface with a release coating such as a silicone release coating as described in U.S. Pat. No. 4,696,854 which is incorporated herein by reference. One suitable release coating is a 100% solids electron beam curable silicone such as TEGO® Resin Acrylates/RC-Series RC 705 and RC 726 by Goldschmidt Chemical Corporation of Hopewell, Va. The preferred backing sheet 10 is a porous polymeric water insoluble nonwoven fibrous fabric. A suitable sizing material for bonding the fibers together is a latex resin.

The backing sheet 10 can comprise other stable, water insoluble flexible sheet materials. One preferred backing comprises a 5.5 mil. strip of nonwoven fabric formed from a mixture of cellulose fibers derived from wood pulp and polyester fibers. The fibers are assembled loosely into the backing to maintain porosity. A unifying or sizing resin is applied to hold the fibers together. The sizing resin can comprise a nonirritating resin applied as a latex emulsion. One example is HYCAR® 26477, a resin produced by B. F. Goodrich Co. of Brecksville, Ohio. Another suitable backing sheet is a nonwoven fabric comprising a wetlay cellulose and polyester nonwoven fabric containing as a sizing an acrylic latex emulsion resin, e.g., product number N7601 by Dexter Corporation of Windsor Locks, Conn.

In another embodiment of the invention, the backing sheet 10 comprises a porous woven 5 mil. acetate polymer cloth sometimes known as "silk cloth." Another form of backing sheet 10 is an open-cell plastic foam strip of low density polyethylene or polyvinyl acetate resin. Other backing sheets that can be used include woven cotton cloth or other cloth formed from a synthetic polymer. Suitable synthetic cloths include nylon, polyester, polyacetate. When the backing sheet 10 is a woven cloth, no sizing resin is needed. The backing sheet 10 is pervious to air so that the patch is non-occlusive to the skin.

The porosity of the backing sheet 10 is important because it provides openings for receiving the hydrocolloidal medication-containing reservoir and it helps to assure that the patch is non-occlusive to the skin. The infusion of the pressure-sensitive hydrocolloidal medication-containing reservoir into the backing sheet 10 is accomplished by controlling manufacturing parameters so as to keep the hydrocolloid sufficiently fluid to prenetrate the backing sheet 10 in spite of its tendency to thicken rapidly when applied. In order to prevent the consistency of the hydrogel from building too fast, i.e., becoming too viscous to properly penetrate the backing sheet 10, a continuous processing mixer 16 (FIG. 1) which includes rotating auger 18 is chilled to help remove heat produced during mixing and keep the hydrogel cool until applied to the backing 10. This can be accomplished by providing the processing mixer 16 with a cooling jacket through which a coolant such as a chilled mixture of water and ethylene glycol is passed during operation. The components of the hydrogel are continuously added to the mixer 16 during operation. While any suitable mixer 16 can be used, one suitable mixer is a five-inch continuous processing mixer manufactured by Teledyne Readco Company of York, Pa. The coolant passed through the processing mixer 16 can be maintained at about 0° C. The temperature of the fluid hydrogel 20 as it flows onto the exposed surface of the backing sheet 10 is important for controlling the infiltration of the coating into the backing sheet 10. The coolant will, under typical operating conditions, keep the extruded hydrogel 20 at a temperature of about 9° C. to 14° C. as it comes into contact with the backing 10. If deeper penetration is desired, the temperature of the hydrogel is lowered to about 9° C. for a typical hydrogel formulation. If less penetration is wanted, the temperature is raised closer to 15° C.

The hydrogel produced by the processing mixer 16, which is in a chilled fluid condition, is expelled at 20 onto the exposed upper surface of the backing sheet 10 adjacent to a knife blade 22 of a knife coater which is held in spaced relationship above a rotatable support roll 23. The distance between the knife 22 and the roll 23 is controlled in any suitable manner, as by means of adjustment screws (not shown) or, if desired, the desired gap or spacing between the knife 22 and roll 23 can be preset to accommodate the backing sheet 10 and the thickness of the hydrogel coating 24 that is being applied to the exposed surface of the backing sheet 10.

In accordance with the invention, the medication-containing hydrogel 20 is applied so as to penetrate a substantial portion of the backing sheet 10, e.g., typically between one-fourth to nine-tenths the thickness of the backing sheet 10. The penetration of the coating 24 into the backing 10 can be seen in FIG. 5. In this case the hydrogel coating 24 has penetrated about three-fourths of the way through the backing sheet 10 to provide an upper, i.e., internal layer 24a of hydrocolloidal material within the pores between the fibers making up the porous backing sheet 10. The hydrogel material thus includes two layers as seen in FIG. 5; the external coating layer 24 with an exposed pressure-sensitive surface 24b and the upper internal portion 24a which infiltrates and becomes solidified within the backing in the interstices between the fibers that make up the porous backing sheet 10.

In one product with very good characteristics the backing sheet 10 is 5.5 mils in thickness and the external part of the coating layer 24 is 8 mils in thickness to provide a combined thickness for the patch when applied to the body of 13.5 mils. The external hydrogel layer 24 is purposely maintained relatively thin. The hydrocolloidal adhesive reservoir infiltrates into the backing to a depth of about 2–5 mils to provide a total hydrocolloid layer, including both the internal and external portions, of about 10–13 mils. Because of its thickness, the medication-containing reservoir provides a very adequate supply of medication to assure sustained release of the medication over an extended period of time, e.g., six to eight hours or more. During use, the medication in the internal reservoir portion 24a stored within the backing sheet 10 migrates from within the backing sheet 10 through the external coating layer 24 and then passes through the skin to provide sustained release of the medication into the body of the patient.

After the hydrogel layer 24 is applied to the backing 10, the backing sheet continues moving toward the right as seen in FIG. 1 into close proximity with an oven or heater, in this case a radiant electric heater 25 which radiates heat onto the hydrogel coating layer 24, raising its temperature to about 140° F. and causing it to cure, i.e., to set up as a solid that is sufficiently stable to maintain its own shape and resist flow during storage or use. Once the heater 25 has warmed the hydrogel coating 24, it will be solidified and dimensionally stable. A liner sheet 26 such as polyethylene coated paper is then applied continuously by pressing it onto the exposed surface of the hydrogel layer 24 as the liner sheet 26 passes beneath a rotating roll 28. The assembled laminate 34 then moves further toward the right in the figure where a die press 30 stamps separate patches 32 from the sheet material.

The hydrogel 20, 24 comprises a hydrocolloidal dispersion of a hydrophilic natural or synthetic gel-forming polymer, a hydrophilic humectant, a biomedically active substance or medication, i.e., a medicament, and a hydrophilic adhesive substance such as an aqueous dispersion of an acrylic adhesive.

The polymer can comprise a natural gum such as gum karaya, gum acacia, locust bean gum, guar gum, or other polysaccharide as well as synthetically formulated polysaccharides, e.g., modified guar gum, maltodextrin, or celluloses such as carboxymethyl cellulose and carboxypropyl cellulose. The polymer can also comprise a synthetic polymer such as polyacrylamide and its cogeners or polyacrylic acid. Polyacrylamide is sold under the trademark "POLYTEC31X" by Tecna Corp., Belleville, N.J.

The humectant can comprise a polyhydric alcohol such as glycerol, propylene glycol, ethylene glycol, or sorbitol.

The adhesive can comprise any suitable biocompatible hydrophilic adhesive such as a resin emulsion adhesive, e.g., an acrylate emulsion adhesive or a copolymer of vinyl acetate and dioctyl maleate. The most outstanding results have been achieved with an acrylic emulsion adhesive. Other hydrophilic adhesives that can be used include an acrylic ester copolymer and a vinyl acetate resin.

Any of a variety of topical medications can be used in accordance with the present invention. When the patch is used as an analgesic, these include trolamine salicylate, methyl salicylate, menthol, camphor, eucalyptus oil, spearmint oil, or a combination thereof. In other applications, the medication can include anti-pruritic agents or anti-inflammatory agent such as hydrocortisone, or anesthetic agents such as benzocaine or lidocaine. Also included are non-steroidal anti-inflammatory agents such as ibuprofen, especially the S-iosmer of ibuprofen. Other medications include keratolytic agents such as salicylic acid, and rubefacient agents such as capsicum.

In FIG. 2 the finished patch 32 is seen applied to the surface of the body with the backing 10 exposed and the pressure-sensitive hydrogel layer 24 bonded to the skin.

In FIG. 3 is shown a package containing the finished patch 32 as it appears during shipment and storage. The package 36 comprises a pouch including lower and upper layers of paper 35, 37 or other suitable packaging material such as metal foil coated paper which is sealed to itself along its edges, e.g., at 36a, 36b to provide a sealed pouch containing the finished patch 32.

As shown in FIGS. 4 and 5, the finished patch 32 includes the porous backing 10, the hydrogel coating including the lower, i.e., external hydrogel coating layer 24 and the upper or internal portion 24a that permeates the backing 10. The upper surface 26a of the liner sheet is a release surface for facilitating its removal. Before use, the liner sheet 26 is removed by pulling it off the patch as shown at the right in FIG. 4 to expose the pressure-sensitive surface of the layer 24 which is then applied to the skin as shown in FIG. 2.

During use, the upper or internal reservoir portion 24a that infiltrates the backing 10 and is solidified therein serves to store the medication within the backing 10 so that the medication migrates over time from its location at 24a within the backing 10 through the external coating layer 24 and then passes through the skin to provide sustained release of the medication into the body of the patient.

The porosity of the backing 10 combined with the water compatibility of the hydrocolloidal dispersion also makes the patch non-occlusive so that moisture from the body can evaporate through the patch into the atmosphere. The moisture vapor transmission rate (MVTR) of the skin alone under various conditions is typically from about 70 to about 149 g/m$^2$/24 hr while the medication applying patch of the present invention is about 612 to 1952 g/m$^2$/24 hr. This shows that the invention is non-occlusive because in a given period of time about 8 to 14 times more moisture vapor is transmitted through the patch of the present invention than through the skin. Prior medication-applying patches that employed a rubber backing allow virtually no moisture evaporation from the skin. By contrast, the non-occlusive patch of the present invention will not interfere with moisture evaporation from the skin. This is important because the evaporation of moisture from the skin helps the skin to act in its normal capacity as a barrier to externally applied compounds which, if absorbed in excessive amounts, can produce toxic reactions or skin irritation. The invention thus enables the barrier function of the stratum corneum to be maintained.

When used as an analgesic patch, the present invention provides outstanding results in relieving pain such as arthritis pain and backache pain, as well as muscular aches and strains. Because of the thinness of the patch, it is perceived as being more comfortable, more flexible, less obtrusive and is more acceptable to the patient. The backing 10 is rendered so translucent by infiltration of the hydrocolloidal gel that the patch is very inconspicuous on the skin. The entire thickness of the analgesic patch is about 13.5 mils.

The invention will be better understood by reference to the following examples:

| Example Number | Percentage by Weight | Component |
| --- | --- | --- |
| 1 | 31.8 | Glycerin |
|   | 0.2 | Quaternium-15[1] |
|   | 21 | Propylene Glycol |
|   | 1 | HydroCortisone |
|   | 25 | Karaya |
|   | 21 | HB Fuller 312Oz[2] |
| 2 | 31.8 | Glycerin |
|   | 0.2 | Quaternium-15[1] |
|   | 21.5 | Propylene Glycol |
|   | 25 | Karaya |
|   | 21 | BF Goodrich 26171[3] |
| 3 | 27.72 | Glycerin |
|   | 0.64 | Quaternium-15[1] |
|   | 24.5 | Propylene Glycol |
|   | 0.5 | HydroCortisone |
|   | 24.64 | Karaya |
|   | 21 | BF Goodrich 26222[3] |
| 4 | 27.72 | Glycerin |
|   | 0.64 | Quaternium-15[1] |
|   | 24.64 | Propylene Glycol |
|   | 1 | HydroCortisone |
|   | 25 | Karaya |
|   | 21 | BF Goodrich 26171[3] |
| 5 | 33 | Glycerin |
|   | 18 | Karaya |
|   | 9 | 34x[4] |
|   | 0.5 | HydroCortisone |
|   | 21.5 | Propylene Glycol |
|   | 18 | BF Goodrich 26171[3] |
| 6 | 14 | Methyl Salicylate |
|   | 4 | Camphor |
|   | 6 | Menthol |
|   | 76 | BF Goodrich 26222[3] |
| 7 | 29 | Glycerin |
|   | 16 | Polytec 31x[5] |
|   | 30 | Propylene Glycol |
|   | 1 | HydroCortisone |
|   | 12 | Lodex[6] |
|   | 4 | H2O (deionized) |
|   | 8 | HB Fuller 312Oz[2] |

| Example Number | Percentage by Weight | Component |
|---|---|---|
| 8 | 30.8 | Glycerin |
| | 15.4 | Polytec 31x[5] |
| | 22.8 | Propylene Glycol |
| | 8 | Lidocaine |
| | 12 | Lodex[6] |
| | 3 | H2O (deionized) |
| | 8 | HB Fuller 3120z[2] |
| 9 | 30.8 | Glycerin |
| | 12 | Karaya |
| | 6.4 | Lodex[6] |
| | 8 | 34x[4] |
| | 29.8 | Propylene Glycol |
| | 1 | Capsicum |
| | 12 | Flexcryl 1615[7] |
| 10 | 30.8 | Glycerin |
| | 12 | Karaya |
| | 5.4 | Lodex[6] |
| | 9 | 34x[4] |
| | 25.8 | Propylene Glycol |
| | 12 | HB Fuller 3120z[2] |
| | 5 | Benzocaine |
| 11 | 31.4 | Glycerin |
| | 12.6 | Karaya |
| | 5.2 | Lodex[6] |
| | 8 | 34x[4] |
| | 29.8 | Propylene Glycol |
| | 1 | HydroCortisone |
| | 12 | HB Fuller 3120z[2] |
| 12 | 14 | Methyl Salicylate |
| | 4 | Camphor |
| | 6 | Menthol |
| | 38 | BF Goodrich 26171[3] |
| | 38 | BF Goodrich 26415[3] |
| 13 | 14 | Methyl Salicylate |
| | 4 | Camphor |
| | 6 | Menthol |
| | 45 | BF Goodrich 26415[3] |
| | 31 | BF Goodrich 26222[3] |
| 14 | 17.4 | Methyl Salicylate |
| | 7.5 | Camphor |
| | 5.1 | Menthol |
| | 70 | BF Goodrich 26415[3] |
| 15 | 15.6 | Methyl Salicylate |
| | 6.8 | Camphor |
| | 4.6 | Menthol |
| | 25 | BF Goodrich 26171[3] |
| | 48 | Flexcryl 1615[7] |
| 16 | 19.8 | Karaya |
| | 36.6 | Glycerin |
| | 15.8 | Methyl Salicylate |
| | 2 | Spearmint Oil |
| | 25.8 | HB Fuller 3120z[2] |
| 17 | 19 | Karaya |
| | 37 | Glycerin |
| | 16 | Methyl Salicylate |
| | 2 | Spearmint Oil |
| | 13 | BF Goodrich 26171[3] |
| | 13 | BF Goodrich 26415[3] |
| 18 | 20 | Karaya |
| | 37 | Glycerin |
| | 8 | Methyl Salicylate |
| | 8 | Trolamine Salicylate |
| | 2 | Spearmint Oil |
| | 12.5 | BF Goodrich 26415[3] |
| | 12.5 | BF Goodrich 26222[3] |
| 19 | 15.6 | Methyl Salicylate |
| | 6.8 | Camphor |
| | 4.8 | Menthol |
| | 30 | BF Goodrich 26334[3] |
| | 43 | BF Goodrich 26222[3] |
| 20 | 15 | Trolamine Salicylate |
| | 10 | Menthol |
| | 34 | BF Goodrich 26171[3] |
| | 41 | BF Goodrich 26222[3] |
| 21 | 20.3 | Methyl Salicylate |
| | 6.6 | Menthol |
| | 32.5 | BF Goodrich 26171[3] |
| | 40.6 | BF Goodrich 26222[3] |
| 22 | 15 | Methyl Salicylate |
| | 10 | Menthol |
| | 29 | BF Goodrich 26171[3] |
| | 46 | BF Goodrich 26222[3] |
| 23 | 23 | Karaya |
| | 34 | Glycerin |
| | 11.5 | Methyl Salicylate |
| | 3 | Menthol |
| | 3 | Camphor |
| | 1.5 | Spearmint Oil |
| | 23 | Avery AE259[8] |
| 24 | 22.5 | Karaya |
| | 36 | Glycerin |
| | 16 | Methyl Salicylate |
| | 3 | Spearmint Oil |
| | 8 | BF Goodrich 26222[3] |
| | 14.5 | BF Goodrich 26171[3] |
| 25 | 22.5 | Karaya |
| | 35.9 | Glycerin |
| | 11.8 | Methyl Salicylate |
| | 3.1 | Camphor |
| | 3.1 | Menthol |
| | 1.6 | Spearmint Oil |
| | 22 | BF Goodrich 26415[3] |
| 26 | 24 | Karaya |
| | 34 | Glycerin |
| | 15 | Methyl Salicylate |
| | 2 | Spearmint Oil |
| | 12.5 | BF Goodrich 26171[3] |
| | 12.5 | BF Goodrich 26334[3] |
| 27 | 21 | Karaya |
| | 38 | Glycerin |
| | 15 | Methyl Salicylate |
| | 2 | Spearmint Oil |
| | 12 | BF Goodrich 26415[3] |
| | 12 | BF Goodrich 26334[3] |
| 28 | 23 | Karaya |
| | 37.5 | Glycerin |
| | 13.8 | Methyl Salicylate |
| | 1.7 | Spearmint Oil |
| | 12 | BF Goodrich 26171[3] |
| | 12 | Aroset 1196[9] |
| 29 | 22 | Karaya |
| | 36 | Glycerin |
| | 14.2 | Methyl Salicylate |
| | 1.8 | Spearmint Oil |
| | 3 | Camphor |
| | 11.5 | Aroset 1196[9] |
| | 11.5 | BF Goodrich 26222[3] |
| 30 | 22 | Karaya |
| | 35 | Glycerin |
| | 12 | Methyl Salicylate |
| | 3.2 | Menthol |
| | 3.2 | Camphor |
| | 1.6 | Spearmint Oil |
| | 11 | Avery AE259[8] |
| | 12 | BF Goodrich 26171[3] |
| 31 | 54 | Glycerin |
| | 26 | Karaya |
| | 10 | Flexcryl 1615[7] |
| | 3.3 | Eucalyptus Oil |
| | 6.7 | Menthol |
| 32 | 23.5 | Karaya |
| | 33.5 | Glycerin |
| | 15.7 | Methyl Salicylate |
| | 2.8 | Spearmint Oil |
| | 9.1 | BF Goodrich 26222[3] |
| | 15.4 | BF Goodrich 26171[3] |
| 33 | 22.6 | Karaya |
| | 35.9 | Glycerin |
| | 6 | Methyl Salicylate |
| | 5.9 | Trolamine Salicylate |
| | 3.2 | Camphor |
| | 3.2 | Menthol |
| | 1.5 | Spearmint Oil |
| | 7.5 | BF Goodrich 26222[3] |

| Example Number | Percentage by Weight | Component |
|---|---|---|
| 34 | 14.2 | BF Goodrich 26171[3] |
| | 22 | Karaya |
| | 35 | Glycerin |
| | 16 | Methyl Salicylate |
| | 4 | Menthol |
| | 6 | Camphor |
| | 2 | Spearmint Oil |
| | 9 | BF Goodrich 26415[3] |
| | 6 | BF Goodrich 26171[3] |
| 35 | 20 | Karaya |
| | 33.8 | Glycerin |
| | 0.2 | Quaternimum-15[1] |
| | 16 | Methyl Salicylate |
| | 4 | Menthol |
| | 6 | Camphor |
| | 1.5 | Spearmint Oil |
| | 12 | BF Goodrich 26222[3] |
| | 6.5 | BF Goodrich 26171[3] |
| 36 | 54 | Glycerin |
| | 26 | Karaya |
| | 5 | BF Goodrich 26222[3] |
| | 5 | BF Goodrich 26171[3] |
| | 6.7 | Menthol |
| | 3.3 | Eucalyptus Oil |
| 37 | 53 | Glycerin |
| | 25 | Karaya |
| | 9.5 | Flexcryl 1615[7] |
| | 8.4 | Menthol |
| | 4.1 | Eucalyptus Oil |
| 38 | 46.5 | Glycerin |
| | 8.4 | Menthol |
| | 4.1 | Eucalyptus Oil |
| | 26 | Karaya |
| | 15 | Flexcryl 1615[7] |
| 39 | 16.8 | Menthol |
| | 8.2 | Eucalyptus Oil |
| | 25 | Avery AE259[8] |
| | 34 | Glycerin |
| | 16 | Karaya |
| 40 | 54 | Glycerin |
| | 26 | Karaya |
| | 10 | BF Goodrich 26222[3] |
| | 6.7 | Menthol |
| | 3.3 | Eucalyptus Oil |
| 41 | 54 | Glycerin |
| | 26 | Karaya |
| | 10 | BF Goodrich 26171[3] |
| | 6.7 | Menthol |
| | 3.3 | Eucalyptus Oil |
| 42 | 54 | Glycerin |
| | 31 | Karaya |
| | 5 | Flexcryl 1615[7] |
| | 6.7 | Menthol |
| | 3.3 | Eucalyptus Oil |
| 43 | 54 | Glycerin |
| | 36 | Karaya |
| | 6.7 | Menthol |
| | 3.3 | Eucalyptus Oil |
| 44 | 49 | Glycerin |
| | 26 | Karaya |
| | 15 | BF Goodrich 26171[3] |
| | 6.7 | Menthol |
| | 3.3 | Eucalyptus Oil |
| 45 | 48 | Glycerin |
| | 24.5 | Karaya |
| | 15 | BF Goodrich 26171[3] |
| | 8.4 | Menthol |
| | 4.1 | Eucalyptus Oil |
| 46 | 49.3 | Glycerin |
| | 23.2 | Karaya |
| | 15 | BF Goodrich 26334[3] |
| | 8.4 | Menthol |
| | 4.1 | Salicylic Acid |
| 47 | 50 | Glycerin |
| | 25 | Karaya |
| | 15 | BF Goodrich 26171[3] |
| | 6.7 | Menthol |
| | 3.3 | Eucalyptus Oil |
| 48 | 47 | Glycerin |
| | 20.5 | Karaya |
| | 15 | BF Goodrich 26415[3] |
| | 11.7 | Menthol |
| | 5.8 | Eucalyptus Oil |
| 49 | 49.3 | Glycerin |
| | 23.2 | Karaya |
| | 15 | BF Goodrich 26171[3] |
| | 8.4 | Menthol |
| | 4.1 | Eucalyptus Oil |
| 50 | 47 | Glycerin |
| | 24.8 | Karaya |
| | 6.7 | Menthol |
| | 3.3 | Eucalyptus Oil |
| | 18.2 | Aroset 1196[9] |

Footnotes:
[1]Quaternium-15 is a perservative comprising of azoniaadamantane chloride by Dow Chemical of Palatine, IL.
[2]HB Fuller 3120z is a residual vinyl acetate monomer resin emulsion in water by HB Fuller of Vadnais Heights, MN.
[3]BF Goodrich 26171, 26222, 26334, and 26415 are acrylic ester copolymers of anionic emulsion adhesives by BF Goodrich of Brecksville, OH.
[4]34x is an anionic polyacrylamide by Tecna Corporation of Belleville, NJ.
[5]Polytec 31x is a non-ionic polyacrylamide by Tecna Corporation of Belleville, NJ.
[6]Lodex is a carbohydrate comprising of Malto Dextrin by American Maize-Product Comp of Hammond, IN.
[7]Flexcyrl 1615 is an adhesive of vinyl acetate/dioctylmaleate copolymer by Air Products and Chemical Inc of Allentown, PA.
[8]Avery AE259 is an acrylic polymer latex adhesive by Avery Chemical of Mill Hill, PA.
[9]Areo set 1196 is an acrylic polymer adhesive by Ashland Chemical of Columbus, OH.

Many variations of the present invention within the scope of the appended claims will be apparent to those skilled in the art once the principles described herein are understood.

What is claimed is:

1. A non-occlusive medication-containing adhesive patch to be applied to the skin for releasing medication into the body of a patient comprising, a porous backing layer comprising flexible sheet of water insoluble material to provide support for the patch, a flexible hydrophilic pressure-sensitive adhesive hydrocolloidal gel matrix including a natural or synthetic polymer and a biomedically active substance, said matrix providing a reservoir for the sustained release of the biomedically active substance to be absorbed through the skin into the body of the patient, said hydrocolloidal gel matrix penetrates a lower portion of the backing and the backing has an upper portion that is unpenetrated by the gel matrix, the gel matrix is solidified within the lower portion of the backing and is dimensionally stable whereby the gel matrix partially penetrates the backing and leaves the upper portion of the backing free from the gel, said gel matrix has two portions including:
  a) an external layer with an exposed surface for bonding to the skin and
  b) an internal portion infiltrated within only the lower portion of the porous backing layer, said biomedically active substance is dispersed in a hydrocolloidal gel matrix including said internal portion, and during use the gel matrix releases the biomedically active substance through an exposed surface thereof that is bonded to the skin of the patient, and the backing has an upper surface that is spaced apart from the gel matrix.

2. The adhesive patch of claim 1 wherein the porous backing layer is a nonwoven fabric comprising water insoluble polymeric fibers with spaces therebetween.

3. The adhesive patch of claim 1 wherein the nonwoven fabric comprises a mixture of polyester fibers and cotton fibers.

4. The adhesive patch of claim 1 wherein the matrix comprises a natural or synthetic gel-forming polymer comprising a member selected from the group consisting of gum karaya, gum acacia, locust bean gum, guar gum, modified guar gum, maltodextrin, carboxymethyl cellulose, carboxypropyl cellulose, polyacrylamide and its cogeners, and polyacrylic acid.

5. The adhesive patch of claim 1 wherein the gel matrix includes a humectant that comprises a polyhydric alcohol.

6. The adhesive patch of claim 5 wherein the polyhydric alcohol comprises a member selected from the group consisting of glycerol, propylene glycol, ethylene glycol, and sorbitol.

7. The patch of claim 5 wherein the polyhydric alcohol is selected from the group consisting of glycerin and propylene glycol.

8. The adhesive patch of claim 1 wherein said matrix includes a resin emulsion adhesive.

9. The adhesive patch of claim 8 wherein the resin emulsion adhesive comprises a member selected from the group consisting of acrylate emulsion adhesive, an acrylic ester copolymer, a vinyl acetate resin, and copolymer of vinyl acetate and dioctyl maleate.

10. The adhesive patch of claim 1 wherein the substance is a medication comprising a member selected from the group consisting of trolamine salicylate, methyl salicylate, menthol, camphor, eucalyptus oil, spearmint oil, hydrocortisone, benzocaine, lidocaine, ibuprofen, salicylic acid, and capsicum.

11. The non-occlusive medication-containing adhesive patch of claim 1 wherein said biomedically active substance is at least one of the following: a topical analgesic, an anti-pruritic agent, an anti-inflammatory agent, an anesthetic agent, a keratolytic agent, a rubrefacient agent.

12. A medication-containing adhesive patch for the transdermal delivery of medication into the body of a patient through the skin comprising, a flexible pressure-sensitive adhesive matrix including a natural or synthetic polymer and a biomedically active substance to be absorbed through the skin into the body of the patient, a porous backing for supporting the matrix, said backing comprising a sheet of water insoluble material having an upper surface and a lower surface, said adhesive patch having the following layers proceeding from a lower surface of the adhesive patch to said upper surface of the backing:

a) an external layer of said adhesive matrix that is located below the lower surface of the backing, said external layer having an exposed surface for bonding to the skin of the patient, b) an internal portion of the matrix partially penetrating the backing so as to be infiltrated within only a lower portion of the porous backing layer, c) said backing layer includes a lower filled portion as a layer in which the internal portion of the matrix layer is infiltrated, and d) an upper layer portion of the backing that is free of said matrix, said biomedically active substance is dispersed in both portions of the matrix whereby the matrix releases the biomedically active substance into the skin through said exposed surface thereof, and the backing has an upper surface that is spaced apart from the gel matrix.

13. The transdermal medication-containing adhesive patch of claim 12 wherein the matrix comprises a member selected from the group consisting of gum karaya, gum acacia, locust bean gum, guar gum, modified guar gum, maltodextrin, carboxymethylcellulose, carboxypropylcellulose, polyacrylamide and its cogeners, polyacrylic acid, vinyl acetate resin, acrylic ester copolymer, carbohydrate, vinyl acetate/dioctyl maleate copolymer, and acrylic polymer.

14. The medication-containing adhesive patch of claim 12 wherein the patch is coated on said upper surface with a release coating.

15. The medication-containing adhesive patch of claim 14 wherein the release coating is silicone.

16. The medication-containing adhesive patch of claim 12 wherein the porous backing layer is a member selected from the group consisting of nonwoven fabric, woven cloth fabric, and open-cell plastic foam.

17. The medication-containing adhesive patch of claim 12 wherein said matrix includes a hydrophilic hydrocolloid, a humectant, and a polymeric adhesive.

18. The medication-containing adhesive patch of claim 17 wherein the hydrophilic hydrocolloid comprises a member selected from the group consisting of gum karaya, gum acacia, locust bean gum, guar gum, modified guar gum, maltodextrin, carboxymethylcellulose, carboxypropylcellulose, polyacrylamide and its cogeners, and polyacrylic acid.

19. The adhesive patch of claim 17 wherein the humectant comprises a member selected from the group consisting of propylene glycol and glycerin.

20. The adhesive patch of claim 17 wherein the polymeric adhesive comprises an acrylic.

21. The adhesive patch of claim 20 wherein said acrylic is an acrylic ester copolymer.

22. The adhesive patch of claim 20 wherein the biomedically active substance comprises a member selected from the group consisting of trolamine salicylate, methyl salicylate, menthol, camphor, eucalyptus oil, spearmint oil, hydrocortisone, benzocaine, lidocaine, ibuprofen, salicylic acid, capsicum, anti-pruritic agents, anti-inflammatory agents, keratolytic agents, and rubefacient agents.

23. A medication-containing adhesive patch for the transdermal delivery of medication into the body of a patient through the skin comprising, a flexible pressure-sensitive adhesive hydrocolloidal gel matrix including a natural or synthetic hydrophilic polymer and a biomedically active substance to be absorbed through the skin into the body of the patient, a polyhydric alcohol selected from the group consisting of glycerin and propylene glycol dispersed in the matrix, a hydrophilic resin emulsion adhesive dispersed in the matrix, said biomedically active substance comprises a member selected from the group consisting of capsicum, eucalyptus oil and spearmint, a porous backing for supporting the matrix, said backing comprising a sheet of water insoluble material having an upper surface and a lower surface, said adhesive patch having the following layers proceeding from a lower surface of the adhesive patch to said upper surface of the backing:

a) an external layer of said adhesive matrix that is located below the lower surface of the backing, said external layer having an exposed surface for bonding to the skin of the patient,
   b) an internal portion of the matrix partially penetrating the backing so as to be infiltrated within only a lower portion of the porous backing layer,
   c) said backing layer includes a lower filled portion as a layer in which the internal portion of the matrix layer is infiltrated, and
   d) an upper layer portion of the backing that is free of said matrix, said biomedically active substance is dispersed in both portions of the matrix whereby the matrix releases the biomedically active substance into the skin through said exposed surface thereof, and the backing has an upper surface that is spaced apart from the gel matrix.

24. A medication-containing adhesive patch for the transdermal delivery of medication into the body of a patient through the skin comprising, a flexible pressure-sensitive adhesive hydrocolloidal gel matrix including a natural or synthetic hydrophilic polymer and a biomedically active substance to be absorbed through the skin into the body of the patient, said polymer comprises a natural or synthetic polysaccharide, a humectant comprising a polyhydric alcohol dispersed in said matrix, a hydrophilic resin emulsion adhesive dispersed in the matrix, the biomedically active substance comprises a member selected from the group of methyl salicylate, spearmint oil, camphor, eucalyptus oil, menthol, trolamine salicylate, and capsicum, a porous backing for supporting the matrix, said backing comprising a sheet of water insoluble material having an upper surface and a lower surface, said adhesive patch having the following layers proceeding from a lower surface of the adhesive patch to said upper surface of the backing:
   a) an external layer of said adhesive matrix that is located below the lower surface of the backing, said external layer having an exposed surface for bonding to the skin of the patient,
   b) an internal portion of the matrix partially penetrating the backing so as to be infiltrated within only a lower portion of the porous backing layer,
   c) said backing layer includes a lower filled portion as a layer in which the internal portion of the matrix layer is infiltrated, and
   d) an upper layer portion of the backing that is free of said matrix, said biomedically active substance is dispersed in both portions of the matrix whereby the matrix releases the biomedically active substance into the skin through said exposed surface thereof, and the backing has an upper surface that is spaced apart from the gel matrix.

* * * * *

UNITED STATES PATENT AND TRADEMARK OFFICE
CERTIFICATE OF CORRECTION

PATENT NO. : 5,536,263
DATED      : Jul. 16, 1996
INVENTOR(S) : Rolf et al.

It is certified that error appears in the above-indentified patent and that said Letters Patent is hereby corrected as shown below:

Col. 10, line 61 (Claim 1), after "dispersed in", change "a" to ---the---.

Col. 11, line 6 (Claim 3), change "1" to ---2---.

On the title page, Col. 2, correct the attorney's name from "James V. Warmon" to ---James V. Harmon---.

Signed and Sealed this

Fifteenth Day of October, 1996

Attest:

BRUCE LEHMAN

Attesting Officer

Commissioner of Patents and Trademarks

US005536263C1

(12) EX PARTE REEXAMINATION CERTIFICATE (5748th)
United States Patent
Rolf et al.

(10) Number: US 5,536,263 C1
(45) Certificate Issued: Apr. 24, 2007

(54) NON-OCCLUSIVE ADHESIVE PATCH FOR APPLYING MEDICATION TO THE SKIN

(75) Inventors: David Rolf, Minneapolis, MN (US); Elisabeth K. S. Urmann, St. Paul, MN (US)

(73) Assignee: Lectec Corporation, Minnetonka, MN (US)

Reexamination Request:
No. 90/005,877, Dec. 7, 2000

Reexamination Certificate for:
Patent No.: 5,536,263
Issued: Jul. 16, 1996
Appl. No.: 08/219,982
Filed: Mar. 30, 1994

Certificate of Correction issued Oct. 15, 1996.

(51) Int. Cl.
*A61F 13/00* (2006.01)

(52) U.S. Cl. ............... 604/307; 424/449; 424/447; 604/304; 514/953; 514/965; 602/48

(58) Field of Classification Search ......... 604/304–307; 424/443–449; 602/41–43, 48
See application file for complete search history.

(56) References Cited

U.S. PATENT DOCUMENTS

| | | | | |
|---|---|---|---|---|
| 2,137,169 | A | 11/1938 | Levey | 167/84 |
| 3,249,109 | A | 5/1966 | Maeth et al. | 128/268 |
| 3,339,546 | A | 9/1967 | Chen | 128/156 |
| 3,428,043 | A | 2/1969 | Shepherd | 128/268 |
| 3,598,122 | A | 8/1971 | Zaffaroni | 128/268 |
| 3,612,053 | A | 10/1971 | Pratt | 128/283 |
| 3,640,741 | A | 2/1972 | Etes | 106/170 |
| 3,731,683 | A | 5/1973 | Zaffaroni | 128/268 |
| 3,742,951 | A | 7/1973 | Zaffaroni | 128/268 |
| 3,767,784 | A | 10/1973 | Gluck | 424/28 |
| 3,814,095 | A | 6/1974 | Lubens | 128/260 |
| 3,972,995 | A | 8/1976 | Tsuk et al. | 424/28 |
| 3,998,215 | A | 12/1976 | Anderson et al. | 128/2.06 E |
| 4,002,221 | A | 1/1977 | Buchalter | 181/0.5 |
| 4,089,329 | A | 5/1978 | Couvillon, Jr. et al. | 128/2 T |
| 4,125,110 | A | 11/1978 | Hymes | 128/2.06 E |
| 4,243,656 | A | 1/1981 | Walliczek | 424/28 |
| 4,253,460 | A | 3/1981 | Chen et al. | 128/283 |
| 4,274,420 | A | 6/1981 | Hymes | 128/641 |

(Continued)

FOREIGN PATENT DOCUMENTS

| | | |
|---|---|---|
| EP | 0 072 251 A2 | 2/1983 |
| EP | 0156565 | 10/1985 |

OTHER PUBLICATIONS

"External Analgesic Drug Products for Over–the Counter Use; Tentative Final Momograph", *Federal Register,* (Feb. 8, 1983).

*Primary Examiner*—Bibhu Mohanty

(57) ABSTRACT

A non-occlusive medication patch to be applied to the skin includes a porous self-supporting backing layer to give the patch the required integrity and strength by acting as a supporting framework for other components, and a flexible hydrophilic pressure-sensitive adhesive reservoir comprising a hydrocolloidal gel for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication-containing reservoir. The medication within the reservoir migrates over time from within the backing through the lower coating layer and passes through the skin to provide sustained release of the medication into the body of a patient. The reservoir comprises a hydrocolloidal dispersion of a natural or synthetic gel-forming polymer, a hydrophilic adhesive, a hydrophilic humectant and a biomedically active medication, i.e, a medicament, dispersed throughout the reservoir including both the external portion and the internal portion that infiltrates the porous backing.

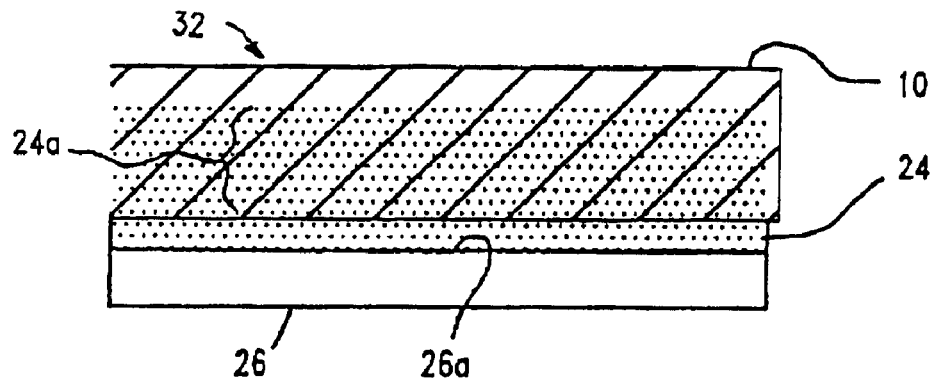

U.S. PATENT DOCUMENTS

| | | | |
|---|---|---|---|
| 4,299,231 A | 11/1981 | Karmann et al. | 128/639 |
| 4,306,551 A | 12/1981 | Hymes et al. | 128/156 |
| 4,307,717 A | 12/1981 | Hymes et al. | 128/156 |
| 4,452,892 A | 6/1984 | Rosevear | 435/176 |
| 4,457,748 A | 7/1984 | Lattin et al. | 604/20 |
| 4,474,570 A | 10/1984 | Ariura et al. | 604/20 |
| 4,515,162 A | 5/1985 | Yamamoto et al. | 128/640 |
| 4,585,652 A | 4/1986 | Miller et al. | 424/83 |
| 4,593,053 A | 6/1986 | Jevne et al. | 523/111 |
| 4,638,043 A | 1/1987 | Szycher et al. | 528/75 |
| 4,668,564 A | 5/1987 | Orchard | 428/246 |
| 4,675,009 A | 6/1987 | Hymes et al. | 604/304 |
| 4,692,273 A | 9/1987 | Lawrence | 252/518 |
| 4,694,835 A | 9/1987 | Strand | 128/640 |
| 4,696,854 A | 9/1987 | Ethier | 428/287 |
| 4,702,732 A | 10/1987 | Powers et al. | 604/20 |
| 4,704,282 A | 11/1987 | Campbell et al. | 424/449 |
| 4,717,378 A | 1/1988 | Perrault et al. | 604/20 |
| 4,725,439 A | 2/1988 | Campbell et al. | 424/449 |
| 4,778,786 A | 10/1988 | Reever et al. | 514/54 |
| 4,803,078 A | 2/1989 | Sakai | 424/445 |
| 4,867,982 A | 9/1989 | Campbell et al. | 424/449 |
| 4,989,607 A | 2/1991 | Keusch et al. | 128/640 |
| 5,002,792 A | 3/1991 | Vegoe | 472/2 |
| 5,120,544 A | 6/1992 | Henley | 424/443 |
| 5,123,423 A | 6/1992 | Scharnberg | 128/798 |
| 5,124,157 A | 6/1992 | Colley et al. | 424/448 |
| 5,142,817 A | 9/1992 | Rolf | 47/24 |
| 5,175,052 A | 12/1992 | Tokuda et al. | 428/355 |
| 5,205,297 A | 4/1993 | Montecalvo et al. | 128/798 |
| 5,224,967 A | 7/1993 | Rolf et al. | 47/58 |
| 5,423,737 A | 6/1995 | Cartmell et al. | 602/57 |
| 5,501,661 A | 3/1996 | Cartmell et al. | 602/58 |
| 5,522,878 A | 6/1996 | Montecalvo et al. | 607/152 |
| 5,536,263 A | 7/1996 | Rolf et al. | 604/307 |
| 5,589,192 A | 12/1996 | Okabe et al. | 424/486 |
| 5,741,510 A | 4/1998 | Rolf et al. | 424/448 |

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 12 and 23–24 are determined to be patentable as amended.

Claims 2–11 and 13–22, dependent on an amended claim, are determined to be patentable.

New claims 25–60 are added and determined to be patentable.

1. A non-occlusive medication-containing adhesive patch to be applied to the skin for releasing medication into the body of a patient comprising[,]:
   a porous backing layer comprising flexible sheet of water insoluble material to provide support for the patch,
   a flexible hydrophilic pressure-sensitive adhesive hydrocolloidal gel matrix including a natural or synthetic polymer and a biomedically active substance, said matrix providing a reservoir for the sustained release of the biomedically active substance to be absorbed through the skin into the body of the patient,
   said hydrocolloidal gel matrix penetrates a lower portion of the backing and the backing has an upper portion that is unpenetrated by the gel matrix, [the] *and said hydrocolloidal* gel matrix is solidified, *including* within the lower portion of the backing, and is dimensionally stable [whereby the gel matrix partially penetrates the backing and leaves the upper portion of the backing free from the gel,] *such that*
   said gel matrix has two portions including:
   a) an external layer with an exposed surface for bonding to the skin and
   b) an internal portion [infiltrated within only the lower portion] *penetrating between one-fourth to nine-tenths of the thickness* of the porous backing layer,
   said biomedically active substance is dispersed in the hydrocolloidal gel matrix including said internal portion,
   *said patch being non-occlusive so that moisture from the body can evaporate through the patch into the atmosphere at a moisture vapor transmission rate of about 612 to 1952 g/m²/24 hr,* and
   during use the gel matrix releases the biomedically active substance through an exposed surface thereof that is bonded to the skin of the patient, and the backing has an upper surface that is spaced apart from the gel matrix.

12. A *non-occlusive* medication-containing adhesive patch for the transdermal delivery of medication into the body of a patient through the skin comprising,
    a flexible pressure-sensitive adhesive matrix including a natural or synthetic polymer and a biomedically active substance to be absorbed through the skin into the body of the patient,
    a porous backing for supporting the matrix, said backing comprising a sheet of water insoluble material having an upper surface and a lower surface,
    said adhesive patch having the following layers proceeding from a lower surface of the adhesive patch to said upper surface of the backing:
    a) an external layer of said adhesive matrix that is located below the lower surface of the backing, said external layer having an exposed surface for bonding to the skin of the patient,
    b) an internal portion of the matrix partially penetrating *between one-fourth and nine-tenths of the thickness of* the backing [so as to be infiltrated within only a lower portion of the porous backing layer],
    c) said backing layer includes a lower filled portion as a layer in which the internal portion of the matrix is [infiltrated] *present*, and
    d) an upper layer portion of the backing that is free of said matrix,
    said biomedically active substance is dispersed in both portions of the matrix whereby the matrix releases the biomedically active substance into the skin through said exposed surface thereof, and
    the backing has an upper surface that is spaced apart from the gel matrix, *said patch being non-occlusive so that moisture from the body can evaporate through the patch into the atmosphere at a moisture vapor transmission rate of about 612 to 1952 g/m²/24 hr.*

23. A *non-occlusive* medication-containing adhesive patch for the transdermal delivery of medication into the body of a patient through the skin comprising,
    a flexible pressure-sensitive adhesive hydrocolloidal gel matrix including a natural or synthetic hydrophilic polymer and a biomedically active substance to be absorbed through the skin into the body of the patient,
    a polyhydric alcohol selected from the group consisting of glycerin and propylene glycol dispersed in the matrix,
    a hydrophilic resin emulsion adhesive dispersed in the matrix,
    said biomedically active substance comprises a member selected from the group consisting of capsicum, eucalyptus oil and spearmint,
    a porous backing for supporting the matrix, said backing comprising a sheet of water insoluble material having an upper surface and a lower surface,
    said adhesive patch having the following layers proceeding from a lower surface of the adhesive patch to said upper surface of the backing:
    a) an external layer of said adhesive matrix that is located below the lower surface of the backing, said external layer having an exposed surface for bonding to the skin of the patient,
    b) an internal portion of the matrix [partially] penetrating *between one-fourth to nine-tenths of the thickness of* the backing [so as to be infiltrated within only a lower portion of the porous backing layer],
    c) said backing layer includes a lower filled portion as a layer in which the internal portion of the matrix is [infiltrated] *present*, and
    d) an upper layer portion of the backing that is free of said matrix,
    said biomedically active substance is dispersed in both portions of the matrix whereby the matrix releases the biomedically active substance into the skin through said exposed surface thereof, and the backing has an upper surface that is spaced apart from the gel matrix, *said patch being non-occlusive so that moisture from the body can evaporate through the patch into the atmosphere at a moisture vapor transmission rate of about 612 to 1952 g/m²/24 hr.*

24. A *non-occlusive* medication-containing adhesive patch for the transdermal delivery of medication into the body of a patient through the skin comprising, a flexible pressure-sensitive adhesive hydrocolloidal gel matrix including a natural or synthetic hydrophilic polymer and a biomedically active substance to be absorbed through skin into the body of the patient, said polymer comprises a natural or synthetic polysaccharide, a humectant comprising a polyhydric alcohol dispersed in said matrix, a hydrophilic resin emulsion adhesive dispersed in the matrix, the biomedically active substance comprises a member selected from the group of methyl salicylate, spearmint oil, camphor, eucalyptus oil, menthol, trolamine salicylate, and capsicum, a porous backing for supporting the matrix, said backing comprising a sheet of water insoluble material having an upper surface and a lower surface, said adhesive patch having the following layers proceeding from a lower surface of the adhesive patch to said upper surface of the backing:

a) an external layer of said adhesive matrix that is located below the lower surface of the backing, said external layer having an exposed surface for bonding to the skin of the patient, b) an internal portion of the matrix partially penetrating *between one-fourth to nine-tenths of the thickness of* the backing [so as to be infiltrated within only a lower portion of the porous backing layer], c) said backing layer includes a lower filled portion as a layer in which the internal portion of the matrix is [infiltrated] *present*, and d) an upper layer portion of the backing that is free of said matrix, said biomedically active substance is dispersed in both portions of the matrix whereby the matrix releases the biomedically active substance into the skin through said exposed surface thereof, and the backing has an upper surface that is spaced apart from the gel matrix, *said patch being non-occlusive so that moisture from the body can evaporate through the patch into the atmosphere at a moisture vapor transmission rate of about 612 to 1952 g/m²/24 hr.*

25. The adhesive patch of claim 12, wherein the backing layer comprises a nonwoven fabric.

26. The adhesive patch of claim 12, wherein the backing layer comprises a nonwoven fabric having polymeric fibers.

27. The adhesive patch of claim 12, wherein the backing layer comprises polyester, cotton or cellulose fibers bonded together with a sizing resin.

28. The adhesive patch of claim 12, wherein the backing layer comprises a porous polymeric water insoluble nonwoven fibrous fabric.

29. The adhesive patch of claim 12, wherein the backing layer comprises a woven fabric.

30. The adhesive patch of claim 12, wherein the backing layer comprises a porous woven acetate polymer cloth, an open-cell plastic foam strip of low density polyethylene or polyvinyl acetate resin, woven cotton cloth, a cloth formed from a synthetic polymer, a cloth formed from nylon, a cloth formed from polyester, or a cloth formed from polyacetate.

31. *The adhesive patch of claim 12, wherein the synthetic polymer comprises a synthetically formulated polysaccharide.*

32. *The adhesive patch of claim 12, wherein the synthetic polymer comprises a synthetically formulated polysaccharide selected from the group of modified guar gum, maltodextrin, cellulose, carboxymethyl cellulose, and carboxypropyl celluloses.*

33. *The adhesive patch of claim 12, wherein the synthetic polymer comprises a synthetic polymer selected from the group of polyacrylamide, cogeners of polyacrylamide, and polyacrylic acid.*

34. *The adhesive patch of claim 12, wherein the internal portion comprises a humectant that comprises a polyhydric alcohol.*

35. *The adhesive patch of claim 34, wherein the humectant comprises a polyhydric alcohol selected from the group of glycerol, propylene glycol, ethylene glycol, and sorbitol.*

36. *The adhesive patch of claim 12, wherein the adhesive matrix comprises a resin emulsion adhesive, an acrylate emulsion adhesive a copolymer of vinyl acetate and dioctyl maleate, an acrylic ester copolymer, or a vinyl acetate resin.*

37. *The adhesive patch of any one of claims 1, 12, 23, and 24, wherein the biomedically active medication comprises an analgesic, an anti-pruritic agent, an anti-inflammatory agent, an anesthetic agent, a non-steroidal anti-inflammatory agent, a keratolytic agent, a rubefacient agent, or a combination thereof.*

38. *The adhesive patch of any one of claims 1, 12, 23, and 24, wherein the biomedically active medication comprises an analgesic.*

39. *The adhesive patch of any one of claims 1, 12, 23, and 24, wherein the biomedically active medication comprises an anti-pruritic agent.*

40. *The adhesive patch of any one of claims 1, 12, 23, and 24, wherein the biomedically active medication comprises an anti-inflammatory agent.*

41. *The adhesive patch of any one of claims 1, 12, 23, and 24, wherein the biomedically active medication comprises an anesthetic agent.*

42. *The adhesive patch of any one of claims 1, 12, 23, and 24, wherein the biomedically active medication comprises a non-steroidal anti-inflammatory agent.*

43. *The adhesive patch of any one of claims 1, 12, 23, and 24, wherein the biomedically active medication comprises a keratolytic agent.*

44. *The adhesive patch of any one of claims 1, 12, 23, and 24, wherein the biomedically active medication comprises a rubefacient agent.*

45. *The adhesive patch of any one of claims 1, 12, 23, and 24, wherein the biomedically active medication comprises an analgesic for the relief of arthritis pain, backache, or muscular aches and strains.*

46. *The adhesive patch of any one of claims 1, 12, 23, and 24, wherein the biomedically active medication comprises trolamine salicylate, methyl salicylate, menthol, camphor, eucalyptus oil, spearmint oil, hydrocortisone, benzocaine, lidocaine, ibuprofen, the S-isomer of ibuprofen, salicylic acid, capsicum, or any combination thereof.*

47. *The adhesive patch of any one of claims 1, 12, 23, and 24, wherein the biomedically active medication comprises trolamine salicylate.*

48. *The adhesive patch of any one of claims 1, 12, 23, and 24, wherein the biomedically active medication comprises methyl salicylate.*

49. The adhesive patch of any one of claims 1, 12, 23, and 24, wherein the biomedically active medication comprises menthol.

50. The adhesive patch of any one of claims 1, 12, 23, and 24, wherein the biomedically active medication comprises camphor.

51. The adhesive patch of any one of claims 1, 12, 23, and 24, wherein the biomedically active medication comprises eucalyptus oil.

52. The adhesive patch of any one of claims 1, 12, 23, and 24, wherein the biomedically active medication comprises spearmint oil.

53. The adhesive patch of any one of claims 1, 12, 23, and 24, wherein the biomedically active medication comprises hydrocortisone.

54. The adhesive patch of any one of claims 1, 12, 23, and 24, wherein the biomedically active medication comprises benzocaine.

55. The adhesive patch of any one of claims 1, 12, 23, and 24, wherein the biomedically active medication comprises lidocaine.

56. The adhesive patch of any one of claims 1, 12, 23, and 24, wherein the biomedically active medication comprises the S-isomer of ibuprofen.

57. The adhesive patch of any one of claims 1, 12, 23, and 24, wherein the biomedically active medication comprises salicylic acid.

58. The adhesive patch of any one of claims 1, 12, 23, and 24, wherein the biomedically active medication comprises capsicum.

59. The adhesive patch of any one of claims 1, 12, 23, and 24, wherein the biomedically active medication comprises an analgesic selected from the group of trolamine salicylate, methyl salicylate, menthol, camphor, eucalyptus oil, spearmint oil, and combinations thereof.

60. The adhesive patch of any one of claims 1, 12, 23, and 24, wherein the biomedically active medication comprises benzocaine, lidocaine, S-ibuprofen, ibuprofen, NSAID's or any combination thereof.

* * * * *